(12) United States Patent
Jui et al.

(10) Patent No.: US 8,039,038 B2
(45) Date of Patent: Oct. 18, 2011

(54) PROCESS FOR THE PREPARATION OF PROTEIN MEDIATED CALCIUM HYDROXYAPATITE (HAP) COATING ON METAL SUBSTRATE

(75) Inventors: Chakraborty Jui, West Bengal (IN); Bharati Sanghamitra, West Bengal (IN); Sinha Mithlesh Kumar, West Bengal (IN); Basu Debabrata, West Bengal (IN)

(73) Assignee: Council of Scientific and Industrial Research, New Delhi (IN)

( * ) Notice: Subject to any disclaimer, the term of this patent is extended or adjusted under 35 U.S.C. 154(b) by 742 days.

(21) Appl. No.: 12/175,812

(22) Filed: Jul. 18, 2008

(65) Prior Publication Data

US 2009/0181161 A1    Jul. 16, 2009

(30) Foreign Application Priority Data

Aug. 20, 2007  (IN) ............ 1759/DEL/2007

(51) Int. Cl.
*B05D 3/02* (2006.01)
*A61L 27/32* (2006.01)
*A61L 27/46* (2006.01)

(52) U.S. Cl. ........ 427/2.27; 427/318; 427/338; 427/435

(58) Field of Classification Search .......... 427/2.27, 427/318, 338, 435
See application file for complete search history.

(56) References Cited

U.S. PATENT DOCUMENTS

| 2003/0113438 | A1* | 6/2003 | Liu et al. | 427/2.24 |
| 2007/0187857 | A1* | 8/2007 | Riley et al. | 264/41 |

* cited by examiner

*Primary Examiner* — Peter Szekely
(74) *Attorney, Agent, or Firm* — Ladas & Parry LLP

(57) ABSTRACT

This invention provides a process for the preparation of protein mediated calcium hydroxyapatite (HAp) coating on metal substrates particularly on stainless steel (316 L) by biomimetic route, capable of rapid and effective osteointegration with the host tissue following controlled interfacial reactions. For the purpose, calcium deficient, carbonated hydroxyapatite (HAp) coating was developed on metal substrates particularly on stainless steel (316L) alloy through biomimetic route after a surface treatment step using aqueous solution (4-10 wt %) of BSA at room temperature. The coating was characterized with respect to phase composition, crystallinity, morphology and thickness. The protein mediated calcium phosphate ceramic coating is porous (pore dia—100-200 µm) having uniform pore distribution and coverage. There is multifold enhancement in thickness and crystallinity (data provided) of the as-prepared coating. The process in the present invention is designed to mimic the structural and characteristic properties of the biological apatite to expedite osteointegration kinetics and to further improve biocompatibility of the metallic implant.

12 Claims, No Drawings

PROCESS FOR THE PREPARATION OF PROTEIN MEDIATED CALCIUM HYDROXYAPATITE (HAP) COATING ON METAL SUBSTRATE

FIELD OF THE INVENTION

The present invention relates to a process for the preparation of protein mediated calcium hydroxyapatite (HAp) coating on metal substrate. More particularly, the present invention relates to a process for the production of protein mediated hydroxyapatite (HAp) coating on stainless steel (316 L) by biomimetic route using supersaturated simulated body fluid (SBF). Surface treatment of the stainless steel (316 L) substrate with a water soluble biomolecule acts as a pre-organized matrix to induce nucleation and growth of the calcium hydroxyapatite crystals in a controlled reaction environment analogous to the biological apatite. This is to mimic the structural and characteristic properties of biological apatite present in natural bone tissue that in turn enhances biocompatibility and bone bonding properties of the implant.

BACKGROUND OF THE INVENTION

Calcium hydroxyapatite [HAp, $Ca_{10}(PO_4)_6(OH)_2$], the main inorganic component of the hard tissues in bone and teeth, is a member of the apatite family. Biological apatite comprises the mineral phase of calcified tissues (enamel, dentin and bone) and is observed to be carbonate substituted, calcium deficient. They differ from pure HAp in stoichiometry, composition, crystallinity and other physical and mechanical properties. For in vivo application, all metallic biomaterials have to be biocompatible. The difference in corrosion resistance, mechanical properties and commercial availability decides their application area. Metallic materials like titanium (Ti) metal and its alloys, cobalt (Co)-chromium (Cr)-molybdenum (Mo) alloy and stainless steel (316 L) are widely used as orthopedic and dental implants. Among these, titanium alloy exhibits superior corrosion resistance and excellent mechanical properties and gives better performance as a metallic stem of hip-joint prosthesis but because of prohibitive cost it has limited use in under developed or developing countries including India. So, this cannot be the material of choice for common people of our country. As an alternative, stainless steel (316L) (composition: 0.03% carbon, 2% manganese, 17-20% chromium, 12-14% nickel, 2-4% molybdenum and small amounts of phosphorous, sulphur and silicon) is widely used hip joint implant.

Insertion of a biomaterial in a living tissue creates an artificial interface between the living tissue and the biomaterial that may render primary or secondary reactions leading to changes in the biological system and the implant material. Under such circumstances, porous hydroxyapatite coatings that are osteoconductive increase the speed and strength of bone attachment compared to uncoated implants of the same design. Other than this, it shields the metallic implant from environmental attack or leaching effects and thus minimizes adverse reactions. Wide spectra of methods have been applied for coating of HAp on metals and other substrates (ceramics, polymers and composites), e.g., dip, plasma spraying, electrophoretic deposition, sputter coating, hot isostatic pressing and ion assisted sputtering etc. Of these, plasma spraying has been used as a major technique in applying hydroxyapatite coatings on metal implants to improve implant fixation and bone growth. Other than being expensive, it suffers from several drawbacks.

Reference may be made to the publication of Serekian P., 'Hydroxyapatite coatings in orthopedic surgery', pp. 81-97, edited by Geesink R. G. T and Manley M. T., Raven Press Ltd., New York, 1993, wherein the advantages and drawbacks of plasma and flame spraying, electrophoresis, dip coating, magnetron sputtering have been discussed.

Reference may be also be made to Cheang P. and Khor K. A., 'Addressing processing problems associated with plasma spraying of hydroxyapatite coatings', Biomaterials, 17, 537-544, 1996, wherein the problems pertinent to the plasma-sprayed HAp coating has been mentioned to be generation of an amorphous phase along with other non-bioactive calcium phosphate phases. The presence of an amorphous phase in the coating is undesirable because natural bone is crystalline, so integrity of the bone-implant interface is compromised. Mechanical tests show failure of the bone-coating-implant interface occurred due to strong resorption and degradation of the coating with high amorphous phase content. Reference may also be made of Barrere F., Blitterswijk van C. A., Groot de K., Layrolle P., 'Influence of ionic strength and carbonate on the Ca—P coating formation from SBF×5 solution', Biomaterials, 23, 1921-1930, 2002 and Liu Y., Layrolle P., Bruijn de J., Blitterswijk van C. and Groot de K., 'Biomimetic coprecipitation of calcium phosphate and bovine serum albumin (BSA) on titanium alloy', J. Biomed. Mater. Res., 57[3], 327-335, 2001, wherein drawbacks of plasma-sprayed HAp coatings have been related to extremely high processing temperature (>10,000° C.) that could not produce bone like apatite, coat heat-sensible complex shaped porous implants or incorporate biologically active molecules such as osteogenic agents and growth factors that increase bone regeneration and have osteo-inductive effect.

Recently, an emerging technique, called biomimetic coating overcomes all the intrinsic drawbacks of the plasma-spraying method. It elaborates a dense, uniform and homogeneous hydroxyapatite (bone-like, carbonate substituted, calcium deficient) coating on metal substrates under mild conditions of pH and at room temperature, in simulated body fluid (SBF) that has similar inorganic composition as human blood plasma. Before applying coating, the substrates are preferably cleaned or treated to remove any surface contaminants and to promote good adhesion of the coating. The metallic implants may be rinsed with a degreaser such as acetone, alkyl alcohols etc. followed by using deionised water. To improve coating adhesion, mechanical surface treatments e.g., sand blasting, scouring, polishing and grinding increase surface roughness and improve bond strength between coating and substrate. Chemical surface treatments are also applied with similar purposes. Acid etching using strong mineral acids e.g., hydrofluoric, hydrochloric, sulfuric, nitric, perchloric or oxidising agents like nitric acid, peroxyhalogen acid, hydrogen peroxide etc. form a fresh bioactive metal oxide layer. After the mechanical or chemical treatment, the surface contaminants are removed by rinsing the implant with deionised water under ultrasound.

Reference may be made to U.S. Pat. No. 5,068,122, Kokubo T., Yamamuro T. and Yoshio A., 'Process for forming a bioactive hydroxyapatite film', 1991, wherein a process for applying a bioactive hydroxyapatite film on inorganic, metallic or organic implant substrates by soaking an assembly comprising a glass (CaO and $SiO_2$) facing a substrate at a predetermined distance apart in an aqueous solution supersaturated with constituent ions of hydroxyapatite has been discussed. In the method according to the present invention, it is not necessary to provide an assembly of glass facing the substrate to be coated.

Reference may be made to U.S. Pat. No. 6,569,489, Li P., 'Bioactive ceramic coating and method', 2003, wherein a bioactive bone mineral (dense, carbonated apatite, crystal size<1 μm) is chemically bonded to a variety of substrates (silicon, metals, ceramics, and polymers), for application in orthopedic and dental prostheses. This coating (thickness 0.005 to 50 μm) is applied uniformly to substrate surfaces of varying geometry and surface textures. It is firmly secured to the substrate and encourages rapid and effective bone ingrowth. The coating is applied by immersing the substrate in an aqueous solution containing calcium, phosphate and carbonate ions (pH range 5-10, temperature<100° C.). Other ions, such as sodium, potassium, magnesium, chloride, sulfate, and silicate, may optionally be present in the solution. The solution is exposed in a controlled environment when it reacts with the substrate to form the coating. The synthetic bone apatite film produced by this process, results in an effective bone composition that promotes bone ingrowth and thereby provides implants with bone-bonding properties. The synthetic apatite film can also be used to attract biological molecules such as growth factors for further improvement of bone growth.

Reference may be made to U.S. Pat. No. 6,733,503, Layrolle P. J. F., de Groot K., de Bruijn J. D., van Blitterswijk C. A., Huipin Y., 'Method for coating medical implants', 2004, wherein a bioactive carbonated calcium phosphate layer for coating the surface of medical implants (stainless steel, titanium, nickel, cobalt, chrome, niobium, molybdenum, zirconium, tantalum and their alloys, alumina, zirconia, bioactive glasses, calcium phosphates) has been provided in an improved bioreactor or fermentor system. After cleaning and acid etching, soaking the implantable device into highly concentrated calcifying solution at low temperature produces the coating. Calcium, phosphate, magnesium, carbonate and additionally sodium chloride salts are dissolved in water by bubbling carbon dioxide gas that increases pH and saturation until there is nucleation of the carbonated calcium phosphate crystals on the surface of the implantable device.

Reference may be made to U.S. Pat. No. 6,692,790, Liu Y., Groot de K., Layrolle and P. J. F., 'Proteinaceous coating', 2004, wherein an implant material (stainless steel, titanium, nickel, cobalt, chrome, niobium, molybdenum, zirconium, tantalum and their alloys, alumina, zirconia, bioactive glasses, calcium phosphates) is cleaned and surface treated (acid etching) followed by immersion in an aqueous solution comprising a protein, (albumin, caesin, gelatin, lysosime, fibronectin, fibrin and chitosan) calcium and phosphate ions through which a gaseous weak acid is passed, degassing the solution. The coating is precipitated on the implant followed by submersing the coated implant into a second solution to redissolve the magnesium, calcium and phosphate ions and to obtain the proteinaceous coating. Here, uniform precipitation of a calcium phosphate layer on the implant surface are formed under modulated nucleation and crystal growth conditions that mimics the way hydroxyapatite crystals are formed in the body. In this method, considering the physiological conditions under which the biomimetic coating is a grown, biologically active agent such as antibiotics can be coprecipitated.

Reference may be made to Jonasova L., Muller F. A., Helebrant A., Strnad J. and Peter G., 'Biomimetic apatite formation on chemically treated titanium', Biomaterials, 25, 1187-1194, 2004, wherein acid etching of the titanium alloy in HCl under inert ($CO_2$) atmosphere for 2 hours was done to obtain a uniform initial substrate surface before alkali treatment. This resulted in formation of a micro-roughened surface and degradation of the passive oxide layer on the titanium alloy (Ti6Al4V) surface, $$TiO_2 + 4HCl \rightarrow TiCl_4 + 2H_2O \qquad (1)$$

Next, alkali treatment with 10 M NaOH at 60° C. for 24 hours resulted in dissolution of the passive $TiO_2$ layer and formation of an amorphous layer containing alkali ions, $$TiO_2 + NaOH \rightarrow HTiO_3^- + Na^+ \qquad (2)$$

When soaked in 1×SBF at 37° C. for 20 days, $Na^+$ ions from the amorphous layer were exchanged by $H_3O^+$ ions from the surrounding fluid resulting in a Ti—OH surface layer formation. This incorporates the $Ca^{2+}$ ions that in turn act as nucleation sites for a homogeneous and thick hydroxycarbonated (HCA) apatite layer formation with bone bonding ability by attaching $(PO_4)^{3-}$ and $(CO_3)^{2-}$ to form Ca—P enriched surface layer. It was seen, thickness of the precipitated HCA layer increased continuously with time.

SBF was prepared by dissolving the reagent grade salts as is mentioned in the above reference (Jonasova L. et al, 'Biomimetic apatite formation on chemically treated titanium', Biomaterials, 25, 1187-1194, 2004), in distilled water and buffered at pH 7.3 with tris-hydroxymethyl aminomethane and HCl at 37° C.

Reference may be made to Song W-H., Jun Y-K., Han Y., Hong S-H., 'Biomimetic apatite coating on micro-arc oxidized titania', Biomaterials, 25, 3341-3349, 2004, wherein biomimetic apatite coatings on micro-arc oxidized titania films were investigated and their apatite-inducing ability was evaluated in both 1×SBF and 1.5×SBF. 1.5×SBF was prepared using the same reagents as above with ion concentrations 1.5 times 1×SBF. When immersed in 1×SBF carbonated hydroxyapatite was induced on the surfaces of the films oxidized at higher voltages (>450V) after 28 days whereas the use of 1.5×SBF reduced the apatite induction time and apatite formation was confirmed even on the surface of the films oxidized at 350 V.

Reference may also be made to Barrere F., Blitterswijk van C. A., Groot de K. and Layrolle P., 'Influence of ionic strength and carbonate on the Ca—P coating formation from SBF×5 solution', Biomaterials, 23, 1921-1930, 2002, wherein biomimetic calcium phosphate coatings were applied on Ti6Al4V alloy using SBF concentrated by a factor 5 (5×SBF) that reduced the soaking time to less than 24 hours. Merck grade reagents were used here and pH was reduced to 6 using $CO_2$ gas at 37° C. Also, it was observed that the coating deposition kinetics is influenced by ionic strength of the solution and $HCO_3^-$ content. $HCO_3^-$ reduces the apatite crystal size of the coating allowing better physical attachment on the titanium alloy substrate. Similarly, reference may be made to Barrere F., Valk van der C. M., Meijer G., Dalmeijer R. A. J., Groot de K., Layrolle P., and 'Osteointegration of biomimetic apatite coating applied onto dense and porous metal implants in femurs of goats', J. Biomed. Mater. Res. Part B: App. Biomaterials, 67B (1), 655-665, 2003, wherein a 30 μm thick carbonated apatitic coating was developed on porous Ti-6Al-4V and tantalum cylinders by immersion into 5×SBF at 37° C. then at 50° C. for 24 hours. These were implanted in the femoral diaphysis of female goats and bone contact was found higher for the above coated implants in comparison to the uncoated implants.

Reference may be made to Tas A. C. and Bhaduri S. B., 'Rapid coating of Ti6Al4V at room temperature with a calcium phosphate solution similar to 10× simulated body fluid', J. Mater. Res., 19[9], 2742-2749, 2004, wherein a 20-65 μm thick bone-like apatitic calcium phosphate coating has been formed on Ti6Al4V substrate at room temperature in 2-6 hours using a super strength solution having concentration of calcium and phosphate ions of human blood plasma/SBF multiplied by a factor of 10. Using a lower concentration (e.g., 1.5×SBF) of SBF, a longer time of two to three weeks is required for the calcium phosphate coating formation in the same method. No buffering agents have been used, instead, prior to coating the pH has been adjusted to 6.5 by addition of sodium bicarbonate. The obtained adhesion strength (12±2 MPa) is comparable to the coating formed by soaking in 1.5×SBF and the Ca/P molar ratio is 1.57.

Reference may also be made to Lin F. H., Hsu Y.-S., Lin S.-H., Sun J.-S., 'The effect of Ca/P concentration and temperature of simulated body fluid on the growth of hydroxyapatite coating on alkali-treated 316 L stainless steel', Biomaterials, 23, 4029-4038, 2002, wherein the importance of stainless steel (316L) in orthopedics and dentistry has been discussed. In this, stainless steel (316L) metallic substrates were soaked in 10 M NaOH (aq. soln.) at 60° C. for 24 hours followed by washing with distilled water and drying at 40° C. for 24 hours in air. These were then heated to 600° C. for 1 hour leading to formation of a thin linking layer of sodium chromium oxide between the HAp coating and the metal substrate. This alkali treated substrate was soaked into SBF (equivalent composition of human blood plasma) at a temperature of 80° C. to yield a dense and uniform bone-like HAp layer on the surface in a period of one week. On increase of calcium and phosphorous ions in the coating, iron oxide and iron chromium oxides were formed on the surface that loosens the HAp layer.

Reference may again be made of Teixeira R. L. P., de Godoy G. C. D. and Pereira M. de M., 'Calcium phosphate formation on alkali-treated titanium alloy and stainless steel', Materials Research, 7[2], 299-303, 2004, wherein biomimetic method has been adopted for coating (calcium phosphate) alkali-treated titanium and stainless steel alloys as an alternative to plasma spraying method. Here, a comparative study has been pursued on biomimetic coating of HAp on alkali treated AISI 316 L and Ti6Al4V alloy substrates. Best results were obtained in 5N sodium hydroxide (NaOH) salt treated (kept at 60° C. for 24 hours) and 20 N NaOH treated stainless steel (kept at 90° C. for 30 minutes). The titanium samples were heat treated at 600° C. for 1 hour and stainless steel samples at 900° C. for ½ hour in air followed by cooling and soaking in SBF at 37° C. for 3 days and in 1.5 SBF at 37° C. for 1 week. This led to the nucleation of a thin (XRD data) calcium phosphate film on the preformed precursors of sodium chromate layer on stainless steel and sodium titanate layer on titanium alloy. An increase in central roughness was noticed with increase in NaOH concentration. This affected the adhesion of the coating through a micro-mechanical adhesion mechanism, though the previous studies have shown that adherence of biomimetic coating increases with alkali treatment of titanium substrates.

Incorporation of biological moieties in the surface treatment step has osteoinductive effect and increase bone regeneration. By suitable choice of concentration of a water-soluble protein, a stable monolayer (held by secondary forces at the inter- and intramolecular level) is adsorbed slowly (evident by the change in pH of the protein solution) on the mechanically roughened (textured) surface of the metal implant at room temperature. This in turn acts as a functionalized template for the nucleation of the requisite calcium phosphate phase (HAp) as a result of electrostatic interactions. The novelty of the present invention lies in development of a single phase HAp coating on the functionalized biomolecular template of the metal substrate at room temperature (35-37° C.). The coating has increased thickness and increased crystallinity of the as-prepared calcium deficient carbonate substituted hydroxyapatite phase. There are alterations in crystal geometry and indication of crystal growth in a preferred orientation. The coating has uniform coverage, porosity and biocompatibility lowering the surface treatment time from more than forty eight hours as is there in the reported processes to only to four hours. Modified crystallinity and physical structure indicates the effect of the underlying biomolecular template that is interfering with the crystal growth and gets incorporated into the mineral latticework. Reference may be made to Wen H. B., Wijn de J. R., Blitterswijk van C. A. and Groot de K., 'Incorporation of bovine serum albumin in calcium phosphate coating on titanium', J. Biomed. Res., 46[2], 245-252, 1999, wherein Ca—P coatings at physiological temperature (37° C.) has been produced on titanium implant materials. This is based on complicated and time consuming wet chemical techniques involving acid etching, boiling diluted alkali incubation followed by immersion in a super saturated calcification solution. Hence, a protein delivery system is produced by coprecipitation of osteogenic proteins (bovine serum albumin) in the coating was chosen in this for coprecipitation and release of biologically active proteins in vivo. Reference may also be made of Liu Y., Layrolle P., Bruijn de J., Blitterswijk van C. and Groot de K., 'Biomimetic coprecipitation of calcium phosphate and bovine serum albumin on titanium alloy', J. Biomed. Res., 57[3], 327-335, 2001, wherein biomimetic coprecipitation of bovine serum albumin (BSA) and calcium phosphate on the titanium alloy surface was done or BSA was deposited onto a biomimetically preformed calcium phosphate matrices. In these methods, no reference of the porosity that is necessary for osteointegration was given therein. Also, the calcium phosphate ceramic coating precipitated on the titanium alloy substrate has been used basically as a carrier system for controlled release of biologically active/osteogenic agents in vivo.

The main drawbacks of the above known art and processes are:
1. Poor coating thickness, a maximum of 65 μm could be achieved in comparison to an average thickness of 100-150 μm in case of plasma-sprayed method
2. Multistep time consuming surface treatment process of the metal substrates
3. Details of porosity parameters (pore size, distribution) of the HAp coating could not be obtained that is necessary for osteointegration
4. Formation of amorphous/poorly crystallized carbonated, calcium deficient hydroxyapatite coating.

OBJECTIVES OF THE INVENTION

The main object of the present invention is to provide a process for the preparation of protein mediated calcium hydroxyapatite (HAp) coating on metal substrates particularly on stainless steel (316 L) by biomimetic route, which obviates the drawbacks detailed as above.

Another object of the present invention is to provide a substantial increase in crystallinity of the as-prepared calcium hydroxyapatite (HAp) coating.

Yet another object of the present invention is to provide an increased coating thickness of the calcium hydroxyapatite (HAp) coating.

Yet another object of the present invention is to reduce the time consumption in the surface treatment step of the process.

Still another object of the present invention is to increase the biocompatibility of the calcium hydroxyapatite coated implant [metal substrate particularly stainless steel (316L)] that may expedite osteointegration kinetics of the implant in vivo.

SUMMARY OF THE INVENTION

Accordingly the present invention provides a process for the preparation of protein mediated calcium hydroxyapatite (HAp) coating on metal substrate and the said process comprising the steps of:
a) roughening and ultrasonic cleaning the surface of the metal substrate by using acetone, ethanol and water by known method to obtain a cleaned metal substrate;
b) drying the above said cleaned metal substrate, at a temperature in the range of 50-60° C., for a period of about 1-2 hours and immersing it in an aqueous solution of protein of concentration in the range of 4-10 wt %, at a temperature in the range of 40-50° C., at pH in the range of 6.5-7, for a period of about 2-4 hours, followed by washing repeatedly 3-4 times with water and drying it at a temperature in the range of 20-30° C., for a period of about 1-2 hours to obtain the dried surface treated metal substrate;
c) immersing the above said dried surface treated metal substrate in a simulated body fluid [SBF(N)], for a period of 1-2 days, at a temperature of 35-37° C., at a pH in the range of 6.5-7 to obtain the nucleated hydroxyapatite coated metal substrate, followed by washing with deionised water for 3-4 times and drying the washed hydroxyapatite nucleated metal, at a temperature in the range of 20-30° C. for a period of about 1-2 hours to obtain the dried hydroxyapatite nucleated metal substrate;
d) immersing the above said dried hydroxyapatite nucleated metal substrate in another simulated body fluid [SBF (O)], for a period in the range of 2-4 days, at temperature of 35-37° C., at a pH in the range of 6-6.5, following by washing with deionised water for 3-4 times and drying it at a temperature of 20-30° C., for a period of 1-2 hours to obtain the desired protein mediated calcium hydroxyapatite (HAp) coating on hydroxyapatite nucleated metal substrate.

In an embodiment of the present invention the metal substrate used is standard steel.

In yet another embodiment of the present invention the roughening of the metal substrate is carried out mechanically by sand blasting, at a pressure of 5-8 kg/cm², for a period of 20-25 seconds.

In yet another embodiment the protein used in step (b) is selected from the group consisting of albumin, caesin, gelatin, lysosime, fibronectin, fibrin, chitosan and collagen.

In yet another embodiment the protein used in step (b) is preferably bovine serum albumin (BSA).

In yet another embodiment the simulated body fluid (N) used for nucleation in step (c) is consisting of the ions:
$Na^+$ in the range of 142-143 mM,
$Cl^-$ in the range of 123-125 mM,
$HCO_3^-$ in the range of 25-27 mM,
$K^+$ in the range of 5-6 mM,
$Mg^{2+}$ in the range of 1.5-1.6 mM,
$Ca^{2+}$ in the range of 2.5-2.6 mM,
$HPO_4^-$ in the range of 1-1.2 mM and
$SO_4^{2-}$ in the range of 0.5-0.6 mM.

In yet another embodiment the simulated body fluid (O) used in step (d) is consisting of the ions:
$Na^+$ in the range of 142-143 mM,
$Cl^-$ in the range of 123-125 mM,
$K^+$ in the range of 5-6 mM,
$Ca^{2+}$ in the range of 2.5-2.6 mM,
$HPO_4^-$ in the range of 1-1.2 mM and
$SO_4^{2-}$ in the range of 0.5-0.6 mM.

In yet another embodiment the inorganic ion concentration (anion and cation) of SBF used in step (c) & (d) is about five times the normal inorganic ion concentration present in simulated body fluid (SBF).

In yet another embodiment the calcium hydroxyapatite coating thickness obtained is in the range of 24-280 µm.

In yet another embodiment the percentage crystallinity of calcium hydroxyapatite coating obtained is in the range of 30-45%.

In still another embodiment the pore size distribution of the porous calcium hydroxyapatite coating obtained is of pore diameter in the range 50-200 µm

DETAIL DESCRIPTION OF THE INVENTION

The present invention involves the use of a water soluble biomolecule in the surface treatment step to induce mineralization of calcium hydroxyapatite ceramic on a metallic implant. This step reduces the total time required for the process substantially. Analogous to the nucleation and growth of calcified bone tissue (biological apatite) in the controlled environment of the oriented collagen fibres, the above work manifests a template (water soluble biomolecule, BSA) directed mineralization of calcium deficient, carbonated HAp (governed by a multitude of secondary interactions) on metal substrates particularly on stainless steel (316L). The presence of such osteogenic protein increases biocompatibility of the implant. Also, no heat treatment step being there in the process, it involves lowest/minimal energy expenses. This indicates viability of the process to that of the reported methods—the purpose is to mimic the superior structural and characteristic properties of the biological apatite so to expedite osteointegration kinetics and improve biocompatibility of the implant material.

The present invention provides a process for production of protein mediated calcium hydroxyapatite (HAp) coating on metal substrates particularly on stainless steel (316 L) by biomimetic route which comprises roughening of metal substrates particularly stainless steel (316 L) sheets in the range of 4-5 µm that was cut in the desired size in the range of (1.5 mm×1.5 mm×1 mm) to (2.5 mm×2.5 mm×1.5 mm) to obtain surface roughened square metal substrates particularly steel plates; ultrasonic cleaning of the surface roughened square metal substrates particularly steel plates using acetone, ethanol and deionized water in that order to obtain cleaned metal substrates particularly steel plates; drying of the cleaned metal substrates particularly steel plates at a temperature in the range of 50-60° C. to obtain dried steel plates; immersing the dried metal substrates particularly steel plates in an aqueous solution of bovine serum albumin (BSA) having volume in the range of 20-30 ml and concentration in the range of 4-10 wt % for a period in the range of 2-4 hours to obtain surface treated metal substrates particularly steel plates; recording pH of the BSA solution before and after immersion of the dried metal substrates particularly steel plates; repeated washing of the surface treated metal substrates particularly steel plates using deionised water for 3-4 times to obtain washed surface treated metal substrates particularly steel plates; drying the washed surface treated metal substrates particularly steel plates at a temperature in the range of 40-50° C. for a period in the range of 1-2 hours to obtain dried surface treated metal substrates particularly steel plates; immersing the dried surface treated metal substrates particularly steel plates in simulated body fluid [SBF (N)] for a period of 1-2 days at a temperature in the range of 35-37° C. to obtain nucleated hydroxyapatite coated metal substrates particularly steel plates; recording pH of the [SBF (N)] before and after immersion of the dried surface treated metal substrates particularly steel plates; repeated washing of the nucleated hydroxyapatite coated metal substrates particularly steel plates using deionised water for 3-4 times to obtain washed hydroxyapatite nucleated metal substrates particularly steel plates; drying the washed hydroxyapatite nucleated metal substrates particularly steel plates at a temperature in the range of 20-30° C. for a period in the range of 1-2 hours to obtain dried hydroxyapatite nucleated metal substrates particularly steel plates; immersing the dried hydroxyapatite nucleated metal substrates particularly steel plates in simulated body fluid [SBF (O)] for a period in the range of 2-4 days at temperature in the range of 35-37° C. to obtain protein mediated calcium hydroxyapatite (HAp) coating on washed hydroxyapatite nucleated metal substrates particularly steel plates; recording pH of the [SBF (O)] before and after immersion of the dried hydroxyapatite nucleated metal substrates particularly steel plates; repeated washing of the protein mediated calcium hydroxyapatite (HAp) coated metal substrates particularly steel plates using deionised water for 3-4 times and drying them at a temperature in the range of 20-30° C. for a period in the range of 1-2 hours to obtain protein mediated calcium hydroxyapatite (HAp) coating on metal substrates particularly on stainless steel (316 L) by biomimetic route.

The process for the production of protein mediated calcium hydroxyapatite (HAp) coating on metal substrates particularly on stainless steel (316 L) by biomimetic route involves the following steps:

1. Metal substrates particularly stainless steel (316L) sheet surface is roughened mechanically and is cut to the shape of square plates having a predetermined dimension.

2. The metal plates are cleaned ultrasonically by known methods as described in open domain.

3. The cleaned plates are immersed in aqueous solution of BSA (4-10 wt %) in a predetermined volume for a period of 2-4 hours to obtain surface treated metal substrates particularly steel plates. Next the plates are washed and dried.

4. The dried plates are immersed in 5×SBF (N) for a period of 2 days at a predetermined temperature followed by washing and drying to obtain hydroxyapatite nucleated metal substrates particularly steel plates.

5. Finally, the dried plates are immersed in 5×SBF (O) for a period of 4 days at a predetermined temperature to obtain an integral, well-formed, continuous hydroxyapatite coating.

The novelty of the present invention lies in the increase in biocompatibility of the end product for use as hip joint, knee joint and dental implant.

The inventive step lies in the surface treatment of metal substrates particularly steel plates (316 L) by immersing in aqueous solution of bovine serum albumin (BSA) having concentration in the range of 4-10 wt %. A consequent final step is the chemical treatment of hydroxyapatite nucleated metal substrates as mentioned in the text. The invention is described with reference to the examples which are provided by way of illustration and therefore should not be construed to limit the scope of the invention.

Example-1

Metal substrates/stainless steel (316L) sheets were surface roughened mechanically in a sand blaster at a pressure of 5 kg/cm$^2$ for a period of 20 seconds. The surface roughness obtained was 4.0 μm. These were cut into the shape of square plates having dimension (1.5 mm×1.5 mm×1 mm). The square metal plates were cleaned ultrasonically using 80 ml each of acetone, ethanol and deionised water in that order taken in a glass beaker for a period of 10 minutes. The cleaned metal plates were dried at a temperature 50° C. for a period of 1 hour. Next, these dried plates were immersed in 20 ml of an aqueous solution (4 wt %) of BSA and kept at 40° C. for a period of 2 hours to obtain surface treated metal plates. Initial and final (after immersion) pH of BSA solution was recorded as 6.95 and 6.85 respectively. These were washed with deionised water 3-4 times and dried at 20° C. in air for 1 hour. Coating thickness of these surface treated plates were measured using a digital micrometer (Mitutoyo digimatic micrometer, Japan) followed by immersing each plate in 40 ml of 5×SBF (N), kept in stoppered PVC [poly(vinyl chloride)] containers at 35° C. in a temperature-controlled bacteriological incubator (Senco, India) for 1 day. Initial and final (after immersion) pH of the 5×SBF (N) was recorded as 5.99 and 6.55. Next, the plates were washed 3-4 times with deionised water and dried at 20° C. in air for 1 hour followed by immersion in 5×SBF (O) at 35° C., in incubator for 2 days. Initial and final (after immersion) pH of the 5×SBF (O) was recorded as 6.11 and 6.23. pH of the SBF and the BSA aqueous solution were measured using a Metler Toledo (Easy seven) digital pH meter. Finally, the plates were washed 3-4 times with deionised water and dried at 20° C. in air for 1 hour. The coating thickness obtained in this case was in the range of 24-25 μm. The percentage crystallinity of the as-prepared HAp coating was determined to be in the range of 30-32%. The pore distribution of the porous HAp coating was not uniform and the pore diameter of the porous HAp coating obtained was in the range 50-80 μm (Table 1).

Example-2

Metal substrates/stainless steel (316L) sheets were surface roughened mechanically in a sand blaster at a pressure of 6 kg/cm$^2$ for a period of 25 seconds. The surface roughness obtained was 4.5 μm. These were cut into the shape of square plates having dimension (2.0 mm×2.0 mm×1.5 mm). The square metal plates were cleaned ultrasonically using 85 ml each of acetone, ethanol and deionised water in that order taken in a glass beaker for a period of 15 minutes. The cleaned metal plates were dried at a temperature 55° C. for a period of one and half hour. Next, these dried plates were immersed in 25 ml of an aqueous solution (6 wt %) of BSA and kept at 45° C. for a period of two and half hours to obtain surface treated metal plates. Initial and final (after immersion) pH of BSA solution was recorded as 6.99 and 6.82 respectively. These were washed with deionised water 3-4 times and dried at 25° C. in air for one and half hour. Coating thickness of these surface treated plates were measured using a digital micrometer (Mitutoyo digimatic micrometer, Japan) followed by immersing each plate in 45 ml of 5×SBF (N), kept in stoppered PVC [poly(vinyl chloride)] containers at 36° C. in a temperature-controlled bacteriological incubator (Senco, India) for one and half days. Initial and final (after immersion) pH of the 5×SBF (N) was recorded as 5.99 and 6.59. Next, the plates were washed 3-4 times with deionised water and dried at 25° C. in air for one and half hours followed by immersion in 5×SBF (O) at 36° C., in incubator for two and half days. Initial and final (after immersion) pH of the 5×SBF (O) was recorded as 6.11 and 6.28. pH of the SBF and the BSA aqueous solution were measured using a Metler Toledo (Easy seven) digital pH meter. Finally, the plates were washed 3-4 times with deionised water and dried at 25° C. in air for one and half hour. The coating thickness obtained in this case was in the range of 50-52 µm. The percentage crystallinity of the as-prepared HAp coating was determined to be in the range of 35-37%. The pore distribution of the porous HAp coating was not uniform and the pore diameter of the porous HAp coating formed obtained was in the range 50-80 µm (Table 1).

Example-3

Metal substrates/stainless steel (316L) sheets were surface roughened mechanically in a sand blaster at a pressure of 7 kg/cm$^2$ for a period of 25 seconds. The surface roughness obtained was 4.8 µm. These were cut into the shape of square plates having dimension (2.0 mm×2.0 mm×1.5 mm). The square metal plates were cleaned ultrasonically using 90 ml each of acetone, ethanol and deionised water in that order taken in a glass beaker for a period of 20 minutes. The cleaned metal plates were dried at a temperature 55° C. for a period of one and half hour. Next, these dried plates were immersed in 25 ml of an aqueous solution (8 wt %) of BSA and kept at 45° C. for a period of 3 hours to obtain surface treated metal plates. Initial and final (after immersion) pH of BSA solution was recorded as 7.01 and 6.85 respectively. These were washed with deionised water 3-4 times and dried at 25° C. in air for one and half hour. Coating thickness of these surface treated plates were measured using a digital micrometer (Mitutoyo digimatic micrometer, Japan) followed by immersing each plate in 45 ml of 5×SBF (N), kept in stoppered PVC [poly(vinyl chloride)] containers at 36° C. in a temperature-controlled bacteriological incubator (Senco, India) for 2 days. Initial and final (after immersion) pH of the 5×SBF (N) and the BSA aqueous solution was recorded as 5.99 and 6.62. Next, the plates were washed 3-4 times with deionised water and dried at 25° C. in air for one and half hour followed by immersion in 5×SBF (O) at 36° C., in incubator for 3 days. Initial and final (after immersion) pH of the 5×SBF (O) was recorded 6.11 and 6.30. pH of the SBF and the BSA aqueous solution were measured using a Metler Toledo (Easy seven) digital pH meter. Finally, the plates were washed 3-4 times with deionised water and dried at 25° C. in air for one and half hours. The coating thickness obtained in this case was in the range of 58-60 µm. The percentage crystallinity of the as-prepared HAp coating was determined to be in the range of 35-32%. The pore distribution of the porous HAp coating was not uniform and the pore diameter of the porous HAp coating obtained was in the range 90-100 µm (Table 1).

Example-4

Metal substrates/stainless steel (316L) sheets were surface roughened mechanically in a sand blaster at a pressure of 7 kg/cm$^2$ for a period of 25 seconds. The surface roughness obtained was 4.8 µm. These were cut into the shape of square plates having dimension (2.0 mm×2.0 mm×1.5 mm). The square metal plates were cleaned ultrasonically using 90 ml each of acetone, ethanol and deionised water in that order taken in a glass beaker for a period of 25 minutes. The cleaned metal plates were dried at a temperature 60° C. for a period of 2 hours. Next, these dried plates were immersed in 30 ml of an aqueous solution (9 wt %) of BSA and kept at 50° C. for a period of three and half hours to obtain surface treated metal plates. Initial and final (after immersion) pH of BSA solution was recorded as 7.05 and 6.89 respectively. These were washed with deionised water 3-4 times and dried at 30° C. in air for two hours. Coating thickness of these surface treated plates were measured using a digital micrometer (Mitutoyo digimatic micrometer, Japan) followed by immersing each plate in 50 ml of 5×SBF (N), kept in stoppered PVC [poly(vinyl chloride)] containers at 37° C. in a temperature-controlled bacteriological incubator (Senco, India) for two days. Initial and final (after immersion) pH of the 5×SBF (N) was recorded as 5.99 and 6.67. Next, the plates were washed 3-4 times with deionised water and dried at 30° C. in air for two hours followed by immersion in 5×SBF (O) at 37° C., in incubator for three and half days. Initial and final (after immersion) pH of the 5×SBF (O) was recorded as 6.11 and 6.32. pH of the SBF and the BSA aqueous solution were measured using a Metier Toledo (Easy seven) digital pH meter. Finally, the plates were washed 3-4 times with deionised water and dried at 30° C. in air for 2 hours. The coating thickness obtained in this case was in the range of 270-275 µm. The percentage crystallinity of the as-prepared HAp coating was determined to be in the range of 42-44%. The pore distribution of the porous HAp coating was uniform and the pore diameter obtained was in the range 100-120 µm (Table 1).

Example-5

Metal substrates/stainless steel (316L) sheets were surface roughened mechanically in a sand blaster at a pressure of 8 kg/cm$^2$ for a period of 25 seconds. The surface roughness obtained was 5 µm. These were cut into the shape of square plates having dimension (2.5 mm×2.5 mm×1.5 mm). The square metal plates were cleaned ultrasonically using 100 ml each of acetone, ethanol and deionised water in that order taken in a glass beaker for a period of 30 minutes. The cleaned metal plates were dried at a temperature 60° C. for a period of 2 hours. Next, these dried plates were immersed in 30 ml of an aqueous solution (10 wt %) of BSA and kept at 50° C. for a period of 4 hours to obtain surface treated metal plates. Initial and final (after immersion) pH of BSA solution was recorded as 7.10 and 6.90 respectively. These were washed with deionised water 3-4 times and dried at 30° C. in air for two hours. Coating thickness of these surface treated plates were measured using a digital micrometer (Mitutoyo digimatic micrometer, Japan) followed by immersing each plate in 50 ml of 5×SBF (N), kept in stoppered PVC [poly(vinyl chloride)] containers at 37° C. in a temperature-controlled bacteriological incubator (Senco, India) for 2 days. Initial and final (after immersion) pH of the 5×SBF (N) was recorded as 5.99 and 6.70. Next, the plates were washed 3-4 times with deionised water and dried at 30° C. in air for 2 hours followed by immersion in 5×SBF (O) at 37° C., in incubator for 4 days. Initial and final (after immersion) pH of the 5×SBF (O) was recorded as 6.11 and 6.35. pH of the SBF and the BSA aqueous solution were measured using a Metler Toledo (Easy seven) digital pH meter. Finally, the plates were washed 3-4 times with deionised water and dried at 30° C. in air for 2 hours. The coating thickness obtained in this case was in the range of 275-280 µm. The percentage crystallinity of the as-prepared HAp coating was determined to be in the range of 44-45%. The pore distribution of the porous HAp coating was uniform and the pore diameter of the porous HAp coating obtained was in the range 120-200 µm (Table 1).

Based on the above examples we can conclude that protein mediated calcium hydroxyapatite (HAp) coating of unique properties can be formed on the metallic substrates particularly stainless steel (316L) by varying different process parameters of the biomimetic route.

TABLE 1

Composition of Simulated Body Fluid (SBF) (N) Solution* used

| SI. No | Ions Present | Conc. (mM) |
|---|---|---|
| 1 | $Na^+$ | 142-143 |
| 2 | $Cl^-$ | 123-125 |
| 3 | $HCO_3^-$ | 25-27 |
| 4 | $K^+$ | 5-6 |
| 5 | $Mg^{2+}$ | 1.5-1.6 |
| 6 | $Ca^{2+}$ | 2.5-2.6 |
| 7 | $HPO_4^-$ | 1-1.2 |
| 8 | $SO_4^{2-}$ | 0.5-0.6 |

*In case of SBF (O) solution, the $Mg^{2+}$, $HCO_3^-$ ions are absent and 5 × SBF (N) solutions have its ion concentrations 5 times as above

TABLE 2

HAp coating thickness, pore size (dia-) distribution and percentage of crystallinity obtained by the process of the present invention

| SI. No. | Conc. Of Protein (wt %) | Coating Thickness of stainless steel(316L) (μm) | Pore size(dia-) of the coating (μm) | % Crystallinity of the as-prepared HAp coating |
|---|---|---|---|---|
| 1 | 1-5 | 20-25 | (50-80), not uniform | 30-32 |
| 2 | 6-8 | 50-60 | (80-100), not uniform | 35-37 |
| 3 | 9-10 | 270-280 | (100-200) uniform distribution | 42-45 |

Advantages of the Invention
1. A substantial reduction of the time in the surface treatment step required for coating of HAp on metal substrates particularly on stainless steel (316L) by biomimetic route.
2. A multifold increase in the coating thickness.
3. Increase in crystallinity of the HAp phase of the coating with alteration in the crystal geometry showing preferred orientation of crystal growth.
4. Uniform porosity (pore dia 100-200 nm) and coverage, that is necessary for osteointegration of the implant.
5. Improvement in biocompatibility (as the nucleation and growth of the HAp crystals take place in a controlled reaction environment analogous to the biological apatite present in natural bone tissue) of the HAp coated implant [metal substrate particularly stainless steel (316L)] that may expedite osteointegration kinetics of the implant in vivo.
6. A simple and cost-effective process with superior coating characteristics.

The invention claimed is:

1. A process for the preparation of protein mediated calcium hydroxyapatite (HAp) coating on metal substrate and the said process comprising the steps of:
   a) roughening and ultrasonic cleaning the surface of the metal substrate by using acetone, ethanol and deionized water by known method to obtain a cleaned metal substrate;
   b) drying the above said cleaned metal substrate, at a temperature in the range of 50-60° C., for a period of about 1-2 hours and immersing it in an aqueous solution of protein of concentration in the range of 4-10 wt %, at a temperature in the range of 40-50° C., at pH in the range of 6.5-7, for a period of about 2-4 hours, followed by washing repeatedly 3-4 times with water and drying it at a temperature in the range of 20-30° C., for a period of about 1-2 hours to obtain the dried surface treated metal substrate;
   c) immersing the above said dried surface treated metal substrate in a simulated body fluid [SBF(N)], for a period of 1-2 days, at a temperature of 35-37° C., at a pH in the range of 6.5-7 to obtain the nucleated hydroxyapatite coated metal substrate, followed by washing with deionised water for 3-4 times and drying the washed hydroxyapatite nucleated metal, at a temperature in the range of 20-30° C. for a period of about 1-2 hours to obtain the dried hydroxyapatite nucleated metal substrate;
   d) immersing the above said dried hydroxyapatite nucleated metal substrate in another simulated body fluid [SBF (O)], for a period in the range of 2-4 days, at temperature of 35-37° C., at a pH in the range of 6-6.5, following by washing with deionised water for 3-4 times and drying it at a temperature of 20-30° C., for a period of 1-2 hours to obtain the desired protein mediated calcium hydroxyapatite (HAp) coating on hydroxyapatite nucleated metal substrate.

2. A process according to claim 1, wherein the metal substrate used is stainless steel.

3. A process according to claim 1, wherein the roughening of the metal substrate is carried out mechanically by sand blasting, at a pressure of 5-8 kg/cm$^2$, for a period of 20-25 seconds.

4. A process according to claim 1, wherein the protein used in step (b) is selected from the group consisting of albumin, casein, gelatin, lysosime, fibronectin, fibrin, chitosan and collagen.

5. A process according to claim 4, wherein the protein used in step (b) is preferably bovine serum albumin (BSA).

6. A process according to claim 1, wherein the simulated body fluid (N) used for nucleation in step (c) is consisting of the ions:
   $Na^+$ in the range of 142-143 mM,
   $Cl^-$ in the range of 123-125 mM,
   $HCO_3^-$ in the range of 25-27 mM,
   $K^+$ in the range of 5-6 mM,
   $Mg^{2+}$ in the range of 1.5-1.6 mM,
   $Ca^{2+}$ in the range of 2.5-2.6 mM,
   $HPO_4^-$ in the range of 1-1.2 mM and
   $SO_4^{2-}$ in the range of 0.5-0.6 mM.

7. A process according to claim 1, wherein the simulated body fluid (O) used in step (d) is consisting of the ions:
   $Na^+$ in the range of 142-143 mM,
   $Cl^-$ in the range of 123-125 mM,
   $K^+$ in the range of 5-6 mM,
   $Ca^{2+}$ in the range of 2.5-2.6 mM,
   $HPO_4^-$ in the range of 1-1.2 mM and
   $SO_4^{2-}$ in the range of 0.5-0.6 mM.

8. A process according to claim 1, wherein the inorganic ion concentration (anion and cation) of SBF used in step (c) & (d) is about five times the normal inorganic ion concentration present in simulated body fluid (SBF).

9. A process according to claim 1, wherein the calcium hydroxyapatite coating thickness obtained is in the range of 24-280 μm.

10. A process according to claim 1, wherein the percentage crystallinity of calcium hydroxyapatite coating obtained is in the range of 30-45%.

11. A process according to claim 1, wherein the pore size distribution of the porous calcium hydroxyapatite coating obtained is of pore diameter in the range 50-200 μm.

12. A process for preparation of protein mediated calcium hydroxyapatite coating on a metal substrate which comprises roughening and cleaning the surface of a metal substrate, applying an aqueous solution of a protein thereto immersing said surface in a first concentrated simulated body fluid (N) containing both magnesium and carbonate ions for a period sufficient to deposit a nucleated hydroxyapatite coating on said surface drying the coated surface and thereafter immersing the surface in a second concentrated simulated body fluid (O) substantially lacking magnesium and bicarbonate ions to obtain a protein mediated calcium hydroxyapatite coating on the substrate.

* * * * *